United States Patent
Kelly et al.

(10) Patent No.: US 10,231,818 B2
(45) Date of Patent: *Mar. 19, 2019

(54) ARTIFICIAL SALIVARY GLAND

(71) Applicant: University of Connecticut, Farmington, CT (US)

(72) Inventors: John Robert Kelly, West Hartford, CT (US); Douglas J. Adams, Farmington, CT (US); Martin Allen Freilich, West Hartford, CT (US)

(73) Assignee: University of Connecticut, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/839,498

(22) Filed: Dec. 12, 2017

(65) Prior Publication Data

US 2018/0110608 A1    Apr. 26, 2018

Related U.S. Application Data

(63) Continuation of application No. 15/080,140, filed on Mar. 24, 2016, now Pat. No. 9,872,757.

(Continued)

(51) Int. Cl.
*A61C 8/00* (2006.01)
*A61F 2/02* (2006.01)
(Continued)

(52) U.S. Cl.
CPC .............. *A61F 2/022* (2013.01); *A61C 8/00* (2013.01); *A61C 8/0018* (2013.01); *A61C 13/08* (2013.01);
(Continued)

(58) Field of Classification Search
CPC ......... A61C 8/00; A61C 8/003; A61C 8/0039; A61C 13/08; A61C 19/06; A61C 19/063; A61F 2/022
See application file for complete search history.

(56) References Cited

U.S. PATENT DOCUMENTS 6,743,626 B2   6/2004   Baum et al.
8,808,202 B2   8/2014   Brancazio
(Continued)

OTHER PUBLICATIONS

Grant et al., Saliva. In: Periodontics, 6th ed., St. Louis: CV Mosby; 1988, pp. 135-146.

(Continued)

*Primary Examiner* — Suba Ganesan
(74) *Attorney, Agent, or Firm* — McCarter & English, LLP

(57) ABSTRACT

Artificial salivary gland devices and assemblies are provided. The present disclosure provides artificial salivary pump/gland devices and assemblies, and related methods of use. One embodiment utilizes the interstitial/marrow fluid reservoir within the underlying mandibular or maxillary bone as a source for replacement saliva. The salivary pump/assembly, which is implantable in the mandibular or maxillary bone as a dental implant and driven by incidental tooth contact and masticatory forces, harvests interstitial/marrow fluid and treats it via semi-permeable membrane technology and soluble particles as a continuously available saliva replacement. Masticatory forces and tooth contact power the pump to both harvest interstitial/marrow fluid and drive flow through a bed of ion-exchange resins and/or soluble particles to adjust fluid chemistry providing a continuously available saliva-like solution. Exemplary devices and assemblies can also be utilized to introduce beneficial bacteria into the oral cavity and/or be utilized as a delivery system for drugs/therapeutic agents.

20 Claims, 11 Drawing Sheets

Related U.S. Application Data

(60) Provisional application No. 62/137,397, filed on Mar. 24, 2015.

(51) Int. Cl.
*A61F 2/28* (2006.01)
*A61C 19/06* (2006.01)
*A61C 13/08* (2006.01)
*A61C 5/50* (2017.01)

(52) U.S. Cl.
CPC .......... *A61C 19/06* (2013.01); *A61C 19/063* (2013.01); *A61F 2/2803* (2013.01); *A61C 5/50* (2017.02); *A61C 8/003* (2013.01); *A61C 8/0039* (2013.01); *A61F 2220/0033* (2013.01)

(56) References Cited

U.S. PATENT DOCUMENTS

| | | |
|---|---|---|
| 9,872,757 B2 | 1/2018 | Kelly |
| 2001/0023324 A1 | 9/2001 | Pronovost et al. |
| 2008/0215010 A1* | 9/2008 | Silver .............. A61C 8/00 604/175 |
| 2013/0123677 A1 | 5/2013 | Ahn |

OTHER PUBLICATIONS

Montgomery et al., Interstitial fluid flow in cortical bone, Microvasc Res (1988); 35:295-307.
Kelly et al., Venous pressure and bone formation, Microvasc Res 1990; 39:364-375.
Tabak, Structure and function of human salivary mucins, Crit Rev Oral Bio and Med 1990, 1(4):229-234.
Dillaman et al., Fluid movement in bone: theoretical and empirical, J Biomech (1991); 24(suppl. 1):163-177.
Hillsley et al., Review: Bone tissue engineering: The role of interstitial fluid flow, Biotech and Bioeng (1994); 43:573-581.
Dowd, Saliva and dental caries, Dent Clin North Am 1999, 43:579-597.
DiResta et al., Aritifical lymphatic system: a new approach to reduce interstitial hypertension and increase blood flow, pH, and $pO_2$ in solid tumors, Annals of Biomed Eng 2000; 28:453-555.
Humphrey et al., A review of saliva:Normal composition, flow and function, J Prosthet Dent 2001; 85(2):162-169.
Frost et al., Patient preferences in a preliminary study comparing intra-oral lubricating device with the usual dry mouth lubricating methods, Br Dent J 2002; 193(7):403-408.
Turner et al., Understanding salivary fluid and protein secretion, Oral Diseases 2002; 8:3-11.
Thompson, Issues in the epidemiological investigation of dry mouth, Gerodontology 2005, 22:65-76.
Al-Nawas et al., Quantifying radioxerostomia: Salivary flow rate, examiner's score, and quality of life questionnaire, Strahlenther Onkol 2006; 182(6):336-341.
de Almeida et al., Saliva composition and functions: A comprehensive review, J Contemp Dent Pract 2008; 9(3):1-11.
Degidi et al., Bone formation around immediately loaded and submerged dental implants with a modified sandblasted and acid-etched surface after 4 and 8 weeks: a human histologic and histomorphometric analysis, In J Oral Maxilofac implants 2009, 24(5):896-901.
Qin et al., Intramedullary pressure and matrix strain induced by oscillatory skeletal muscle stimulation and its potential adaptation, J Biomech (2009); 42(2): 140-145.
Jensen et al., A systematic review of salivary gland hypofunction and xerostomia induced by cancer therapies: prevalence, severity and impact on quality of life, Support Care Cancer 2010; 18:1039-1060.
Furness et al., Interventions for the management of dry mouth: topical therapies, The Cochrane Collaboration, published in The Cochrane Library 2011, Issue 12.
Palmquist et al., Bone-titanium oxide interface in humans revealed by transmission electron microscopy and electron tomography, J R Soc Interface 2012; 9:396-400.
Hu et al., Dynamic hydraulic fluid stimulation regulated intramedullary pressure, Bone (2013); 57:137-141.
PCT Search Report and Written Opinion based on PCT/US2016/024043 dated Jun. 13, 2016.
U.S. Appl. No. 62/137,397, filed Mar. 24, 2015, N/A.
U.S. Appl. No. 15/080,140, filed Mar. 24, 2015, U.S. Pat. No. 9,872,757.

* cited by examiner

ARTIFICIAL SALIVARY GLAND

CROSS-REFERENCE TO RELATED APPLICATIONS

This application is a continuation of U.S. patent application entitled "Artificial Salivary Gland," which was filed on Mar. 24, 2016, and assigned Ser. No. 15/080,140, which claims the benefit of U.S. Provisional Application entitled "Improved Artificial Salivary Gland," which was filed on Mar. 24, 2015, and assigned Ser. No. 62/137,397, the contents of both are herein incorporated by reference in their entireties.

FIELD OF THE DISCLOSURE

The present disclosure relates to salivary gland devices or assemblies and, more particularly, to artificial salivary gland devices or assemblies and related methods of use.

BACKGROUND OF THE DISCLOSURE

As many as 20 million individuals in the U.S. alone cannot make sufficient saliva for normal function and comfort, a condition called xerostomia. The vast majority of these (about 16 million) have xerostomia as a side-effect of prescription medications, another 4 million due to Sjögren's Syndrome and approximately 300,000 become xerostomic each year secondary to head and neck radiation for cancer. Aside from discomfort and pain, related to chronically dry oral mucosa, xerostomia often leads to tooth caries and Candidiasis due to the lack of salivary functions related to enzymatic activity and buffering. Numerous lubricating and saliva substitute products have generally been ineffective in bringing desired relief. (See, e.g., Furness et al., Interventions for the management of dry mouth: topical therapies, The Cochrane Collaboration and published in The Cochrane Library 2011, Issue 12).

Average whole saliva flow in healthy individuals is about 1.0 L to 1.5 L per day (0.7 to 1.0 ml/min). (Humphrey and Williams, A review of saliva: Normal composition, flow and function, J Prosthet Dent 2001; 85(2):162-9). Xerostomia (dry mouth) due to hyposalivation is commonly defined as stimulated flow of less than or equal to 0.2 ml/minute. (Al-Nawas et al., Quantifying radioxerostomia: Salivary flow rate, examiner's score, and quality of life questionnaire, Strahlenther Onkol 2006; 182(6):336-41). As noted, discomfort and pain are related to chronically dry oral mucosa, while increased disease processes are related to the lack of salivary functions which are chemistry dependent.

Disease Background/Unmet Medical Need:

Dry mouth is a common problem with a range of causes. The symptom may be due to a reduction in the quantity of saliva produced, with a feeling of dry mouth. Radiotherapy or chemotherapy for head and neck cancers, and diseases such as Sjögren's Syndrome, may result in reduced saliva production. Many commonly prescribed medications are associated with a feeling of dry mouth, despite normal saliva production. As well as difficulty in speaking, chewing and swallowing, prolonged dry mouth may result in increased risk of tooth decay and reduced quality of life.

Thus, despite efforts to date, a need remains for artificial salivary gland assemblies, and related methods of use. These and other inefficiencies and opportunities for improvement are addressed and/or overcome by the assemblies, systems and methods of the present disclosure.

SUMMARY OF THE DISCLOSURE

The present disclosure provides advantageous salivary gland devices or assemblies. More particularly, the present disclosure provides advantageous artificial salivary gland devices or assemblies, and related methods of use.

The present disclosure provides remedies to the clinical problems noted above. For example, an exemplary embodiment of the present disclosure utilizes fluid (e.g., the interstitial fluid and/or bone marrow fluid reservoir) within jaw bone (e.g., mandibular and/or maxillary bone) as a source for replacement saliva. The present disclosure provides for an exemplary salivary assembly, which is implantable in jaw bone (e.g., mandibular or maxillary bone). This assembly is a dental implant, optionally including a piston head, which may be driven by tooth contact and masticatory forces to harvest fluid (e.g., interstitial and/or bone marrow fluid) filtered via semi-permeable membrane technology as a continuously available saliva replacement. Tooth contact and masticatory forces may power the piston head to both harvest fluid and drive flow through a semi-permeable membrane and optionally through soluble particles to adjust fluid chemistry, thereby providing a continuously available saliva-like solution.

Patients (e.g., patients with xerostomia) can receive a specially designed dental implant member having porous walls and a hollow center for housing replaceable insert members. These insert members can include a piston head, membranes to filter-out materials (e.g., cells and salts), and optionally soluble particles to adjust fluid chemistry (e.g., interstitial and/or bone marrow fluid chemistry) towards that of saliva. Both the initial implant surgery and the insert replacement procedures can be provided in dental offices or the like. Exemplary patients can receive one or more implants (e.g., one to four implants), and can have their insert members replaced at monthly or longer intervals.

In exemplary embodiments, the present disclosure provides assemblies that substantially restore normal saliva flow, along with important salivary functions, especially anti-caries function. The saliva-like fluid can flow at a constant background rate during rest, swallowing with incidental tooth contact and at a higher rate during eating. No other technology can generally restore normal salivary flow.

In exemplary embodiments, the present disclosure provides that harvesting fluid of a user (e.g., interstitial and/or marrow fluid) as a saliva source is novel. Using a dental implant assembly to capture interstitial and/or marrow fluid is novel. Treating interstitial and/or marrow fluid by adjusting its chemistry to be similar to that of saliva is novel (e.g., using semi-permeable membranes). Using muscles of mastication to power a piston member or piston head (e.g., fluid pump) intraorally is novel.

It is also noted that the exemplary devices/assemblies of the present disclosure may also be utilized to introduce beneficial bacteria into the oral cavity and/or be utilized as a delivery system for drugs/therapeutic agents.

The present disclosure provides for a salivary gland assembly including an implant member, the implant member configured and dimensioned to be at least partially disposed within a mouth of a user; and an insert member at least partially disposed within the implant member; wherein the implant member and the insert member are configured and dimensioned to harvest a fluid of the user as a source for replacement saliva for the user.

The present disclosure also provides for a salivary gland assembly wherein the implant member is configured and dimensioned to be at least partially implanted in mandibular or maxillary bone of the user; wherein the fluid is interstitial fluid or marrow fluid; and wherein the implant member and the insert member utilize fluid from a first fluid reservoir within the mandibular or maxillary bone as the source for replacement saliva for the user, and wherein the implant member includes a second fluid reservoir at an apical portion of the implant member, the first fluid reservoir in communication with the second fluid reservoir.

The present disclosure also provides for a salivary gland assembly wherein the implant member and the insert member include porous walls to harvest the fluid; and wherein the insert member is configured to screw or snap fit into the implant member.

The present disclosure also provides for a salivary gland assembly wherein the insert member includes a piston member, the piston member configured to be driven, at least in part, by tooth contact forces of the user to harvest the fluid as the source for replacement saliva for the user. The present disclosure also provides for a salivary gland assembly wherein the piston member is driven, at least in part, by masticatory forces or incidental tooth contact during swallowing forces of the user on the piston member to harvest the fluid as the source for replacement saliva for the user.

The present disclosure also provides for a salivary gland assembly wherein the insert member includes treatment materials to adjust or alter the chemistry of the fluid; and wherein the treatment materials include semi-permeable membranes or soluble particles.

The present disclosure also provides for a salivary gland assembly wherein the piston member is a piston head; and wherein the piston head is in fluid communication with a one-way valve. The present disclosure also provides for a salivary gland assembly wherein the piston member utilizes the tooth contact forces of the user to: (i) harvest the fluid, (ii) drive the fluid to flow through treatment materials to alter or adjust the chemistry of the fluid, and (iii) drive the fluid to an oral cavity of the user.

The present disclosure also provides for a salivary gland assembly wherein the implant member is substantially hollow and the insert member is removable and replaceable from the implant member.

The present disclosure also provides for a salivary gland assembly wherein the insert member includes an outer chamber in fluid communication with the fluid; and wherein when tooth contact forces of the user engage the insert member, the outer chamber is pressurized, thereby causing fluid to flow through the insert member and out of an outlet of the insert member and into an oral cavity of the user. The present disclosure also provides for a salivary gland assembly further including a valve member associated with the insert member; and wherein when the tooth contact forces cease engaging the insert member, the valve member closes and creates a vacuum in the outer chamber, thereby drawing additional fluid of the user into the outer chamber. The present disclosure also provides for a salivary gland assembly wherein the insert member includes one or more spring members; and wherein when the tooth contact forces cease engaging the insert member, the one or more spring members facilitate the closing of the valve member.

The present disclosure also provides for a salivary gland assembly further including a crown member mounted with respect to the insert member, the crown member providing a coronal chewing surface for the user, and providing a chamber configured to house or treat the fluid. The present disclosure also provides for a salivary gland assembly wherein the insert member includes a fluidically-driven piston member in communication with a fluid bladder member of a crown member, the fluid bladder member having an occlusal member mounted on a coronal end of the fluid bladder member; and wherein the fluidically-driven piston member is configured to be driven, at least in part, by tooth contact forces of the user on the occlusal member to harvest the fluid as the source for replacement saliva for the user.

The present disclosure also provides for a salivary gland assembly further including a filter member mounted to an apical end of the insert member, wherein the filter member is in communication with a fluid reservoir of the implant member.

The present disclosure also provides for a salivary gland assembly further including an abutment member, the abutment member configured to be at least partially disposed within the implant member, with the insert member configured to be at least partially disposed within the abutment member and at least partially disposed within the implant member to secure the abutment member, the insert member and the implant member to one another. The present disclosure also provides for a salivary gland assembly further including a crown member mounted on a coronal end of the abutment member, and a piston member mounted on a coronal end of the insert member, the piston member configured to be driven, at least in part, by tooth contact forces of the user to harvest the fluid as the source for replacement saliva for the user. The present disclosure also provides for a salivary gland assembly wherein the insert member is threadably engaged with the implant member to secure the abutment member, the insert member and the implant member to one another.

The present disclosure also provides for a salivary gland assembly including a hollow and substantially cylindrical implant member, the implant member configured and dimensioned to be at least partially implanted in jaw bone of a mouth of a user; and a hollow and substantially cylindrical insert member at least partially disposed within the implant member; wherein the implant member and the insert member are configured and dimensioned to harvest interstitial fluid or marrow fluid of the user as a source for replacement saliva for the user; wherein the implant member and the insert member utilize fluid from a fluid reservoir within mandibular or maxillary bone as the source for replacement saliva for the user; wherein the insert member includes a piston member, the piston member configured to be driven, at least in part, by masticatory forces or incidental tooth contact during swallowing forces of the user on the piston member to harvest the interstitial fluid or marrow fluid as the source for replacement saliva for the user; wherein the insert member includes treatment materials to adjust or alter the chemistry of the interstitial fluid, the treatment materials including semi-permeable membranes or soluble particles; and wherein the piston member utilizes the masticatory forces or incidental tooth contact during swallowing forces of the user to: (i) harvest the fluid, (ii) drive the fluid to flow through the treatment materials to alter or adjust the chemistry of the fluid, and (iii) drive the fluid to an oral cavity of the user.

The present disclosure also provides for a method for harvesting fluid including providing an implant member, the implant member configured and dimensioned to be at least partially disposed within a mouth of a user; and disposing an insert member at least partially within the implant member; wherein the implant member and the insert member are configured and dimensioned to harvest a fluid of the user as a source for replacement saliva for the user.

Any combination or permutation of embodiments is envisioned. Additional advantageous features, functions and applications of the disclosed assemblies, systems and methods of the present disclosure will be apparent from the description which follows, particularly when read in conjunction with the appended figures. All references listed in this disclosure are hereby incorporated by reference in their entireties.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the scope of the present disclosure. To assist those of ordinary skill in the art in making and using the disclosed assemblies, systems and methods, reference is made to the appended figures, wherein.

DETAILED DESCRIPTION OF THE DISCLOSURE

Figure 1:
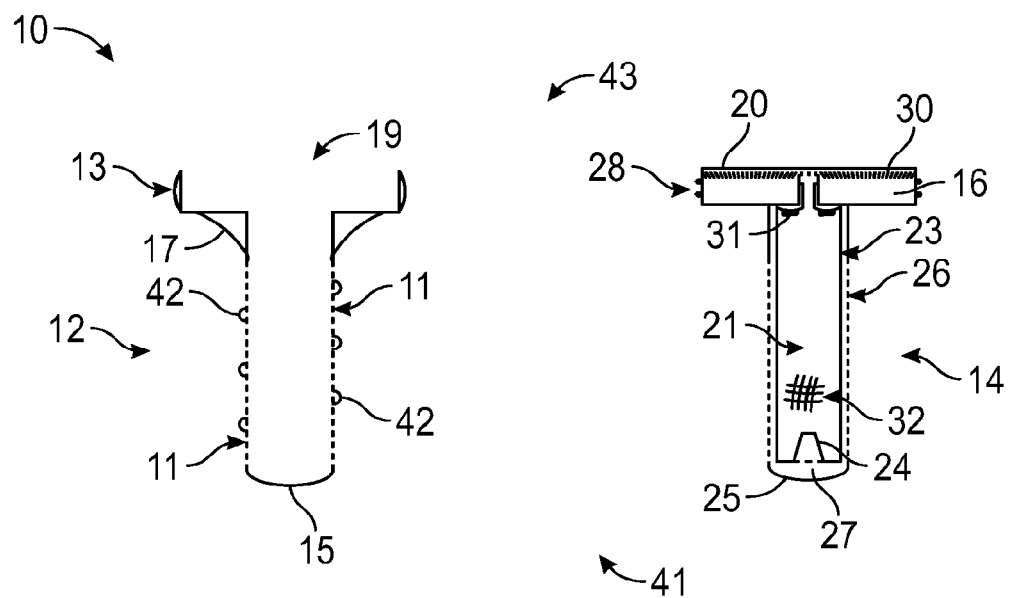
FIG. 1 shows cross-sectional views of an implant member (left) having porous walls to capture bone fluid (e.g., interstitial/marrow fluid); on the right is the replaceable insert member which is configured to be fitted/housed into the implant member, and which can include a piston head and membrane/treatment materials to alter the chemistry of the bone fluid making it more "saliva like" (described in detail below)

The exemplary embodiments disclosed herein are illustrative of advantageous salivary gland assemblies and systems of the present disclosure and methods/techniques thereof. It should be understood, however, that the disclosed embodiments are merely exemplary of the present disclosure, which may be embodied in various forms. Therefore, details disclosed herein with reference to exemplary salivary gland assemblies/systems and associated methods/techniques of assembly and use are not to be interpreted as limiting, but merely as the basis for teaching one skilled in the art of how to make and use the advantageous salivary gland assemblies/systems and/or alternative salivary gland assemblies of the present disclosure.

The present disclosure provides improved salivary gland devices or assemblies. More particularly, the present disclosure provides improved artificial salivary gland devices or assemblies, and related methods of use. In exemplary embodiments, the assemblies of the present disclosure include novel concepts from implant dentistry and from mechanical and chemical engineering. One embodiment of the present disclosure utilizes the interstitial/marrow fluid reservoir within the underlying mandibular or maxillary bone as a source for replacement saliva. The present disclosure provides for an exemplary salivary pumping assembly which is implantable in jaw bone (e.g., the mandibular or maxillary bone) as a dental implant and driven by forces (e.g., masticatory forces) to harvest fluid (e.g., interstitial/marrow fluid) and treat it via semi-permeable membrane technology as a continuously available saliva replacement.

It is also noted that the exemplary devices/assemblies of the present disclosure can also be utilized to introduce beneficial bacteria into the oral cavity and/or be utilized as a delivery system for drugs/therapeutic agents.

Average whole saliva flow is about 1.0 L to 1.5 L per day (Humphrey and Williams, A review of saliva: Normal composition, flow and function, J Prosthet Dent 2001; 85(2): 162-9). Stimulated and un-stimulated rates are found to differ widely as indicated in Table 1 below (Wrigley Practitioner Portal):

TABLE 1

Flow Rates of Whole Saliva
Whole Saliva Flow Rates (ml/min)

|  | Normal Flow Rates | Abnormal Flow Rates |
|---|---|---|
| Unstimulated (Resting) Whole Saliva* | 0.3-0.4 ml/min | <0.1 ml/min |
| Stimulated Whole Saliva* | 1-2 ml/min | <0.5 ml/min |

*Whole saliva is the total output from the major (parotid + submandibular + sublingual) and minor salivary glands.

Xerostomia is commonly defined as stimulated flow of less than or equal to 0.2 ml/min, and is commonly associated with side effects from prescription medicines, Sjögren's Syndrome and post head/neck radiation cancer treatment. Approximately 21% (ranging from 12% to 39%) of non-institutionalized patients in the U.S. have xerostomia, and as many as 4 million patients are living with Sjögren's Syndrome in the United Sates and as many as 300,000 become xerostomic each year due to radiation treatment (Thompson, Issues in the epidemiological investigation of dry mouth, Gerodontology 2005, 22:65-76; see also Jensen et al., A systematic review of salivary gland hypofunction and xerostomia induced by cancer therapies: prevalence, severity and impact on quality of life. Support Care Cancer 2010; 18:1039-1060). Aside from discomfort, pain and disruption of taste, xerostomia often leads to tooth caries and Candidiasis. Discomfort and pain are related to chronically dry oral mucosa, while increased disease processes are related to the lack of salivary functions, which are chemistry dependent.

Salivary Functions and Their Related Chemistry:

Saliva performs many often inter-related functions, many of which are based in the chemistry of dissolved species. These chemical species include anions, cations, proteins, enzymes, carbohydrates, and immunoglobulins. Interestingly, many of these species are commercially available and practical to include in a replacement fluid.

At least five main functions of saliva are: 1) taste; 2) protection and lubrication; 3) buffering and pH modulation; 4) maintenance of mineralization; and, 5) antibacterial and antifungal action. Many of the five major functions of saliva are supported by more than one species and each species is often directly contributing to more than one function or acting in support of another species. (de Almeida et al., Saliva composition and functions: A comprehensive review, J Contemp Dent Pract 2008; 9(3):1-11).

Taste:

Saliva is hypotonic with respect to plasma. (Turner and Sugiya, Understanding salivary fluid and protein secretion, Oral Diseases 2002; 8:3-11). This means that the low levels of glucose, sodium, chloride and urea generally leave some capacity for the dissolution of substances for stimulation of gustatory buds. Gustin is also thought to be involved in the growth and maturation of taste buds.

Protection and Lubrication:

Mucins (e.g., soluble proteins having high carbohydrate content) are largely responsible for maintaining salivary viscosity, protection against dehydration and lubrication. Mastication, speech and deglutition are aided by these proteins. Mucins are complex proteins present as two predominant molecular weight types. (Tabak, Structure and function of human salivary mucins, Crit Rev Oral Bio and Med 1990, 1(4):229-34). Mucins generally have low solubility in water, high viscosity, high elasticity and strong adhesiveness.

Buffering Capacity and Modulation pH:

Bicarbonates, phosphates, urea, amphoteric proteins and enzymes provide these capabilities.

Maintenance of Mineralization (Tooth Integrity):

Calcium and phosphate are maintained in supersaturated concentrations. Statherin, a salivary peptide, contributes to the stabilization of calcium and phosphates in solution, serves as a lubricant to protect against tooth wear, and may initiate the formation of the protective pellicle by binding to hydroxyapatite. (Dowd, Saliva and dental caries, Dent Clin North Am 1999, 43:579-97).

Antibacterial Activities:

These functions are due to the actions of immunoglobulins (principally α-amylase), proteins and enzymes. Mucins also play a supportive role by modulating the adhesion of microorganisms. Lysozymes split bacterial cell walls, leading to the destruction and inhibition of bacterial growth. (Grant et al., Saliva. In: Periodontics, 6th ed., St. Louis: C V Mosby; 1988, P. 135-46). Moreover, lysozymes promote the clearance of bacteria through aggregation.

Exemplary Artificial Salivary Pump/Assembly Concept—Fluid Considerations:

Interstitial and marrow fluid exists in bone at a slightly elevated pressure relative to venous pressure (interstitial fluid discussed in detail below). The ionic content of interstitial fluid differs from that of saliva as seen in Table 2 below:

TABLE 2

|  | Interstitial Fluid | Saliva |
|---|---|---|
| Cations |  |  |
| sodium | 136-145 mmol/L | 2-26 mmol/L |
| potassium | 3-4 mmol/L | 13-40 mmol/L |
| calcium | 1.2-5 mmol/L | 0.5-2.8 mmol/L |
| magnesium | 0.666 mmol/L | 0.15-0.6 mmol/L |
| Anions |  |  |
| chloride | 114 mmol/L | 25 mmol/L |
| phosphate | 0.61 mmol/L | 6 mmol/L |
| bicarbonate | 31 mmol/L | 20 mmol/L |
| sulphate | 1 mmol/L | 1.45 µmol/L |
| organic acid | 7 mEq/L |  |
| Proteins |  |  |
| protein | 1 mEq/L |  |
| mucin |  |  |
| sialin |  |  |
| histatins |  |  |
| Enzymes |  |  |
| α-amylase |  |  |

Balancing Fluid Chemistry Via Semi-Permeable Membrane Technology:

So one challenge, in harvesting interstitial/marrow fluid as a saliva replacement, is to balance the chemistry of dissolved species. For example, both sodium and chloride may be too high, and both phosphate and potassium may be too low. One concept of the present disclosure is to use semi-permeable membranes to remove most dissolved species. Desired normal ionic species can potentially then be replaced by dissolution of soluble granular salts before fluid enters the oral cavity. Replacement rates can be controlled and governed by solubility and particle size. Other normal species such as water soluble proteins (e.g., mucins), enzymes (e.g., amylase), and beneficial species such as fluoride and xylitol can also be added.

In certain embodiments and as discussed further below (FIG. 1), an exemplary salivary gland assembly 10 (e.g., implant-pumping assembly or fluid delivery assembly 10) can include a porous osseo-integrated hollow implant member 12, and an insert member 14 which may include a piston head 16, the insert member 14 having an internal chamber 21 (e.g., an ion exchange chamber 21). In some embodiments, the insert member 14 is removable/replaceable by the clinician.

There is not much evidence from a recent Cochrane Review that topical therapies are effective for relieving the symptom of dry mouth. Many topical treatments (e.g., applied directly to the inside of the mouth) such as sprays, lozenges, mouth rinses, gels, oils, chewing gum or toothpastes have been evaluated in this review, but generally there is no strong evidence that any topical treatment is effective for relieving the sensation of dry mouth. Alternatives such as dentures and night guards with fluid reservoirs have achieved mixed results for night-time use. (Frost et al., Patient preferences in a preliminary study comparing intra-oral lubricating device with the usual dry mouth lubricating methods, Br Dent J 2002; 193(7):403-8).

Estimating Availability of Interstitial Fluid:

Extracellular fluid space in tibial bone (canine) was measured to be approximately 30% (Kelly and Bronk, Venous pressure and bone formation, Microvasc Res 1990; 39:364-375). Thus, approximately 30% of the surface of the exemplary implant will be directly exposed to fluid-filled spaces within the trabecular bone. Implant bone contact is reported to be in the range of either 35% or 75%; apparently depending on measurement technique (Palmquist et al., Bone-titanium oxide interface in humans revealed by transmission electron microscopy and electron tomography, J R Soc Interface 2012; 9:396-400; see also Degidi et al., Bone formation around immediately loaded and submerged implants with a modified roughened surface after 4 and 8 weeks: a human histologic and histomorphometric analysis, In J Oral Maxilofac implants 2009, 24(5):896-901)—hence this is in keeping with the 30% figure for fluid-filled space.

Thus it appears that a volume of interstitial/marrow fluid can be available to draw from and that its replacement rate may be higher than the anticipated withdrawal rate of approximately 0.2 ml/min. It is also noted that interstitial fluid pressure can be positive relative to atmospheric pressure and that pressures may rise during function (e.g., chewing). The extent to which inherent pressures can be used to drive fluid through the insert, or not, will determine the need for a pumping function driven by chewing forces (and the related spring constant). Insights into this will develop from rabbit studies in progress.

Data from exemplary rabbit studies show that sufficient fluid is available to reach approximately 0.7 ml/min for extended times. This fluid reservoir appears to "refresh" continuously.

Figure 3:
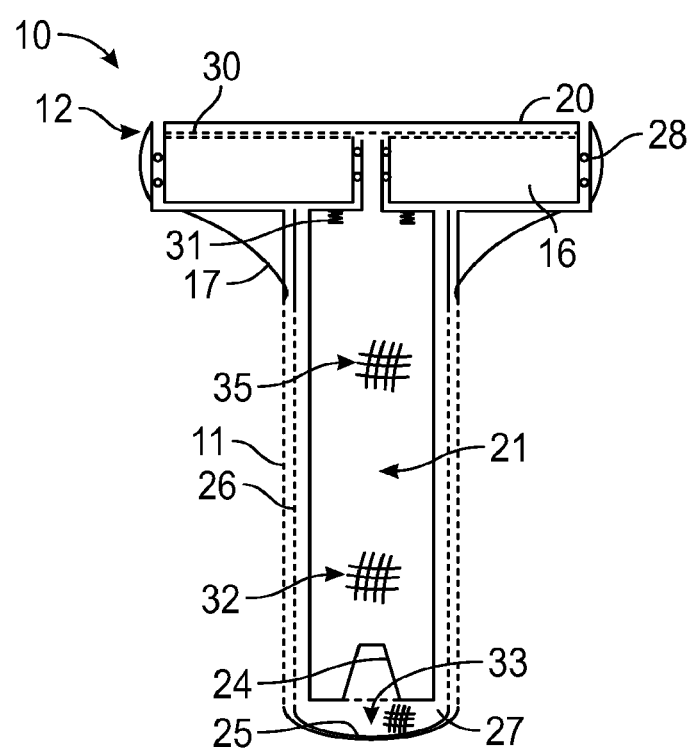
FIG. 3 shows schematic details of a combined implant member with insert member disposed in place.

Artificial Salivary Pump/Assembly Concept—Component and Surgical Considerations:

As noted and as shown in FIGS. 1 and 3, an exemplary salivary gland assembly 10 can include an implant member 12 (e.g., a porous osseo-integrated hollow implant member 12), and can include an insert member 14 (e.g., fluid-processing insert member 14) having a piston head 16, and having a (hollow) internal chamber 21 (e.g., ion exchange chamber 21).

In general and as shown in FIG. 1, implant member 12 and insert member 14 extend from a coronal end 43 to an apical end 41. Exemplary implant member 12 can include external threads on cylindrical portion 15.

As shown in FIG. 1, exemplary salivary gland assembly 10 includes at least two components: (i) an implantable (hollow) implant member 12 having porous walls 11 (e.g., a porous osseo-integrated implant member 12); and (ii) an insert member 14 configured and dimensioned to be disposed or housed in the hollow implant member 12 (e.g., insert member 14 is configured to be screwed or snap-fit into the implant member 12).

Exemplary hollow implant member 12 is substantially cylindrical and includes enlarged coronal cylindrical head portion 13 and apical cylindrical portion 15, the head portion 13 being open 19 at the coronal end 43 and configured to allow insert member 14 to be positioned within implant member 12 (e.g., within hollow head portion 13 and within hollow cylindrical portion 15—FIG. 3). Implant member 12 can also include transmucosal portion 17, and external threads 42.

In some embodiments, the open end 19 of head portion 13 laterally extends about 8.5 mm from a first end to a second end (diameter). For example, open end 19 can be ring-shaped and have a diameter of about 8.5 mm. The lower end of cylindrical portion 15 can have a diameter of about 4.8 mm, although the present disclosure is not limited thereto.

The implanted implant member 12 can osseo-integrate with mandibular or maxillary bone as a dental implant (thus avoiding the problem of fibrous encapsulation seen with other implanted devices). In certain embodiments, during the healing phase this hollow implant member 12 may be filled with blocking material (e.g., in the form of a removable insert attached to a healing abutment member) to substantially obturate the entire internal spaces/portions 13 and/or 15 as well as the pores of wall 11 to prevent filling and blockage with clotted blood during and following surgery. The occlusal opening 19 of the implanted implant member 12 can be closed with an implant healing abutment member. Following osseo-integration, the healing abutment member can be exposed/removed, the blocking material removed from implant member 12, and the fluid-processing insert member 14 can be placed/positioned within implant member 12 (FIG. 3). These components and steps are illustrated in FIGS. 1-4. FIGS. 1-4 show an exemplary implanted implant member 12 having porous walls 11 to capture fluid of a user (e.g., interstitial/marrow fluid).

The exemplary (replaceable) insert member 14 (e.g., substantially cylindrical insert member 14) is configured and dimensioned to be housed, disposed or fitted into the implanted implant member 12.

Exemplary insert member 14 is substantially cylindrical and includes enlarged coronal cylindrical piston head 16 and an apical cylindrical portion 25 extending from piston head 16, the insert member 14 also having a hollow internal chamber 21 (e.g., ion exchange chamber 21) configured to optionally house treatment materials 32, 35 to alter the chemistry of the interstitial fluid making it more "saliva like" (described in detail above).

As shown in FIG. 1, hollow cylindrical portion 25 includes porous walls 26, with the hollow cylindrical portion 25 configured and dimensioned to house the internal chamber 21, and with the cylindrical portion 25 defining an outer chamber 27 between the porous walls 26 and the non-porous walls 23 of internal chamber 21.

Internal chamber 21 can be substantially cylindrical and include non-porous walls 23, and be in fluid communication with a valve member 24 (e.g., one-way valve 24) at the apical end 41, and be in fluid communication with piston head 16 at the coronal end 43, as discussed further below.

As such, exemplary insert member 14 can be substantially cylindrical and includes piston head 16 and cylindrical portions 21, 25, with portions 21, 25 configured to be housed within portion 15 of implant member 12, and with piston head 16 configured to be housed within portion 13 of implant member 12 (FIG. 3). Thus, insert member 14 is configured and dimensioned to be disposed or housed in the hollow implant member 12 (e.g., with the insert member 14 screwed or snap-fit into the implanted implant member 12).

Insert member 14 (e.g., piston head 16 of insert member 14) can also include one or more gasketing members 28 (e.g., O-rings 28) and/or have high tolerances configured to form a fluid-tight seal with head portion 13 (FIG. 3). Moreover and as discussed further below, insert member 14 (e.g., piston head 16 of insert member 14) can also include or be associated with one or more fluid channels 30, and one or more spring members 31 (e.g., spiral stainless steel spring members 31).

Figure 2A:
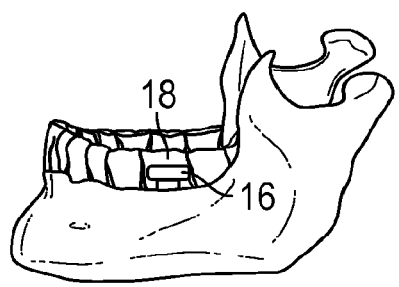
FIG. 2A shows the piston head of the insert member as seen emerging from bone with a tooth-like addition on the coronal end bringing its height up to the occlusal plane.

FIG. 2A shows the piston head 16 of the insert member 14 as emerging from bone, with a crown member 18 (e.g., tooth-like addition 18) mounted on the coronal end bringing its height up to the occlusal plane.

Figure 2B:
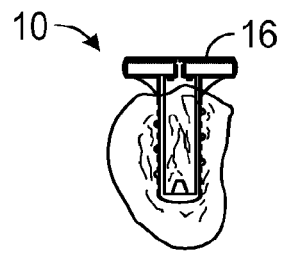
FIG. 2B shows a cross-sectional view of the combined assembly/device placed or implanted within mandibular bone, as a dental implant.

FIG. 2B is a cross-sectional view of the combined dental implant or assembly 10 placed within mandibular bone.

Exemplary details of a combined assembly 10 are illustrated in FIG. 3. As such, FIG. 3 shows the schematic details of a combined implantable implant member 12 with the insert member 14 in place.

In certain embodiments of the present disclosure and as shown in FIG. 3, some exemplary structural components include: (i) a valve member 24 (e.g., one-way valve member 24) controlling fluid flow away from the bone and towards the oral cavity, and (ii) a spring-driven piston head 16 (via springs 31) alternately pressurizing the space or outer chamber 27 between the porous walls 26 and the non-porous walls 23 of internal chamber 21 and developing a vacuum (further illustrated in FIGS. 4A-4B).

Chemical components or treatment materials of assembly 10 can include a bed of activated carbon 33 (e.g., in chamber 27 and beneath the valve 24 to remove soluble organic species), ion-exchange resins 32 (e.g., mixed bed ion exchange resin 32) in the chamber 21 above the valve 24 (e.g., removing Na and Cl), and soluble particles 35 (e.g., mixed cation, anion protein release bed 35 in chamber 21; amorphous calcium phosphate, fluoride, protein release bed 35 in chamber 21) to add additional desired species (e.g., $PO_4$ and K).

Figure 4A:
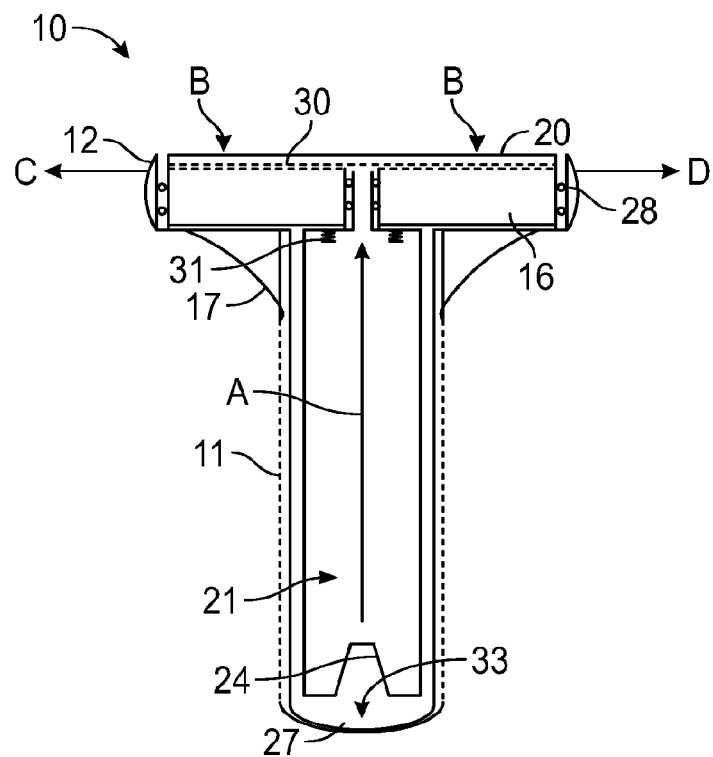
FIG. 4A shows that the forces due to chewing (on coronal end of insert member) pressurize the outer chamber of the insert member, thereby causing fluid to flow through the insert member and into the oral cavity.

FIG. 4A illustrates the action of user forces (e.g., chewing forces, masticatory forces, swallowing with incidental tooth contact, etc.) on the coronal end 20 of piston head 16 to cause pressure in chamber 27 to drive the flow of fluid (e.g., interstitial/marrow fluid) through the one-way valve 24 and into chamber 21, and up through the treatment chamber 21 in the direction of Arrow A and out into the oral cavity via the fluid channels 30 in the piston head 16 of the insert member 14 and in the directions of Arrows C, D.

As such, FIG. 4A shows that coronal forces due to chewing/swallowing or the like (e.g., user chewing forces in the direction of Arrows B on coronal end 20 of piston head 16 of insert member 14) displace or move piston head 16 in the direction of Arrows B and pressurize the outer chamber 27 of the insert member 14, thereby causing fluid flow through the insert member 14 and into an oral cavity of the user. In certain embodiments, when the piston head 16 is moved/displaced in the direction of Arrows B, the springs 31 positioned underneath piston head 16 will compress between piston head 16 and the coronal end of chamber 21, and/or between piston head 16 and a coronal surface of head portion 13.

Figure 4B:
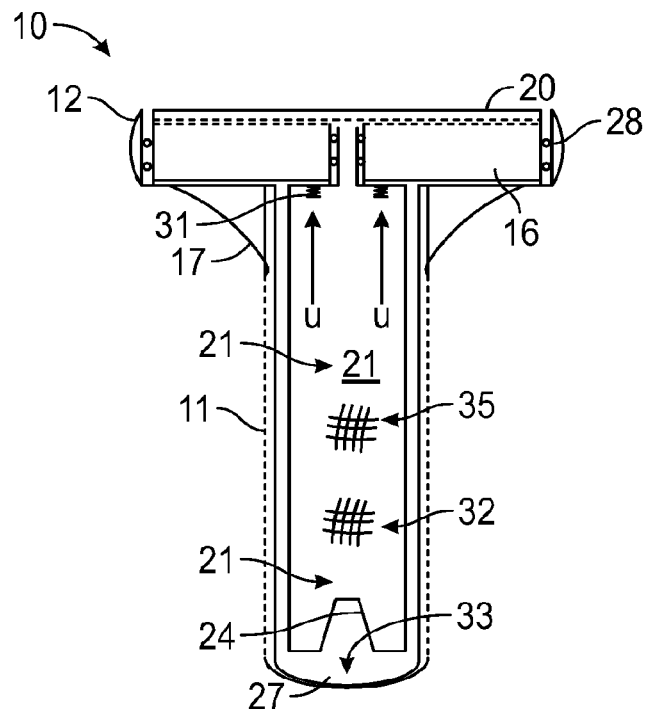
FIG. 4B shows that when chewing forces are removed, upward/apical spring force (below springs) close the one-way valve and create a vacuum in the outer chamber of the insert member, thereby drawing-in fluid (e.g., interstitial/marrow fluid)

As shown in FIG. 4B, when chewing forces are removed, the upward spring force of spring members 31 in the direction of arrows U displace or move piston head 16 in the direction of Arrows U, thereby closing the one-way valve and creating a vacuum in the outer chamber 27 of insert member 14, which thereby draws-in fluid (e.g., interstitial/marrow fluid) into the chamber 27 (e.g., via pores of walls 11, 26).

Thus and as shown in FIG. 4B, when chewing forces are removed, the springs 31 of the insert member 14 will create a vacuum in chamber 27, thereby closing the one-way valve 24 and drawing fluid (e.g., interstitial/marrow fluid) into the outer chamber 27 of the insert member 14.

It is noted that it is possible that there may be sufficient fluid pressure (e.g., interstitial/marrow fluid pressure) to cause a constant fluid flow through assembly 10 to the oral cavity at a reasonable rate without tooth contact, and that chewing or swallowing-driven pumping/movement (e.g., movement of piston head 16) will simply increase saliva flow during chewing/swallowing as happens under normal function. If fluid pressure is too high, resulting in constant flow at too high a rate, resistance in the one-way valve 24 can be increased so that flow only happens during chewing/swallowing or as activated by the patient on demand.

Exemplary Embodiments/Technology

One exemplary masticatory piston head 16 is designed with an active surface area of about 267 $mm^2$ (e.g., coronal end 20 of piston head 16 has an active surface area of about 267 $mm^2$). This is based on a ring-shaped piston head 16 design with an insert member 14 volume displacement of about 7.2 $mm^3$ at a vertical displacement of about 0.2 mm (yielding −80 MPa vacuum). In exemplary embodiments and as noted above, the ring-shaped piston head 16 can be driven with occlusal pressure of the user opposed by the stainless steel spiral springs 31.

Exemplary Evidence:

Design considerations have been worked out and the assembly 10 can be prototyped. From calculations based on practical pump dimensions and also on ion-exchange resin capabilities, this concept of harvesting interstitial/marrow fluid and converting it into faux saliva is shown to be advantageous. Additional evidence includes the formation of bone-to-titanium interfaces in dental implants (e.g., no fibrous tissue encapsulation is expected to block fluid flow), and the plan to replace the inner chamber is expected to ameliorate fouling as well. Sterility can be maintained by some combination of the use of nano-silver coatings and a disinfecting insert.

Bone can be protected with a (permanent) membrane/filter (e.g., millipore membrane/filter) lining the wall 11 of osseo-integrated implant member 12, and/or with a membrane/filter (e.g., millipore membrane/filter or reverse osmosis membrane—Dow Filmtec BW30) lining the wall 26 of insert member 14.

In exemplary embodiments, the present disclosure provides complex medical assemblies/devices 10 fabricated at least in part from titanium and/or a titanium alloy. Exemplary methods can include the fabrication of complicated metal parts (including implantable medical devices/assemblies 10) from 3D computer designs using laser welding or laser machining. Methods can include both the computer design as well as the actual fabrication of prototype and experimental insert members 14 and/or assemblies 10.

Other methods can include the analytical chemistry needed to adjust and optimize ionic and other chemical species between that found in interstitial/bone fluid and in saliva. It is noted that further development can include: small animal studies (rabbit) to further prove the concept that interstitial/marrow fluid is available and obtain initial data on flow versus vacuum pressure; further designing and building a prototype; developing further expertise in ion-exchange resin technology and/or semi-permeable membrane technology; further developing and quantifying chemistry adjustments using the prototype and artificial bone model; further optimization/improvement of design for desired flow rates and maximizing time between replacement of insert member 14; further development of mini-pig trials to evaluate optimized/improved prototype for both function and durability; and a human trial.

Figure 5:
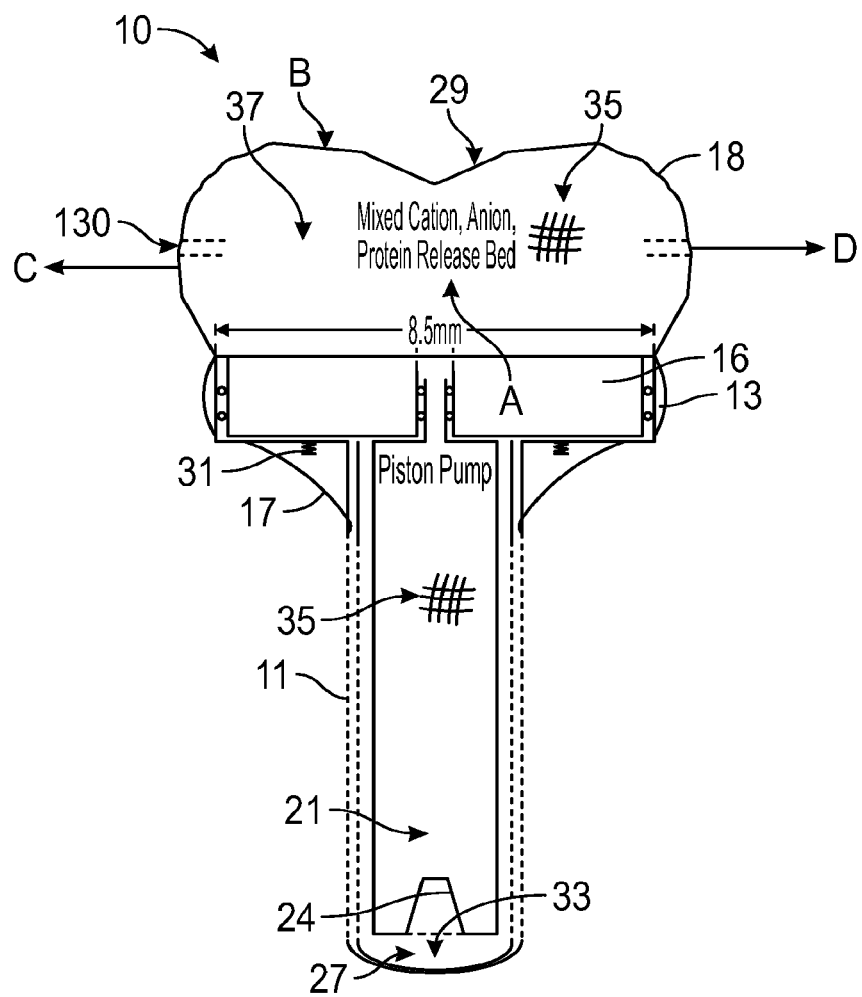
FIG. 5 shows schematic details of a salivary gland assembly having an artificial crown member.

In another embodiment and as shown in FIG. 5, exemplary salivary gland assembly 10 includes a crown member 18 mounted on top of piston head 16 of insert member 14.

As such, the action of user forces (e.g., chewing/swallowing forces of a user) to a coronal surface 29 of crown member 18 causes pressure in chamber 27 to drive the flow of fluid (e.g., interstitial/marrow fluid) through the valve member 24 (e.g., one-way valve 24) and into internal chamber 21, and up through the internal chamber 21 in the direction of Arrow A and out into the oral cavity via the fluid channels 130 in the crown member 18 and in the directions of Arrows C, D, as similarly described above in connection with fluid channels 30 of head 16. It is noted that in this embodiment, piston head 16 may or may not include fluid channels 30.

It is noted that advantageous crown member 18 can provide additional volume via chamber 37 to house treatment materials 35 (e.g., soluble species, such as, for example, proteins, xylitol, amorphous calcium phosphate, etc.).

It is noted that the addition of crown member 18 can more than double the volume over the implant insert member 14. In general, crown member 18 or the like provides that the patient has tooth contacts or during chewing provides pumping forces or movement to piston head 16.

Figure 6:
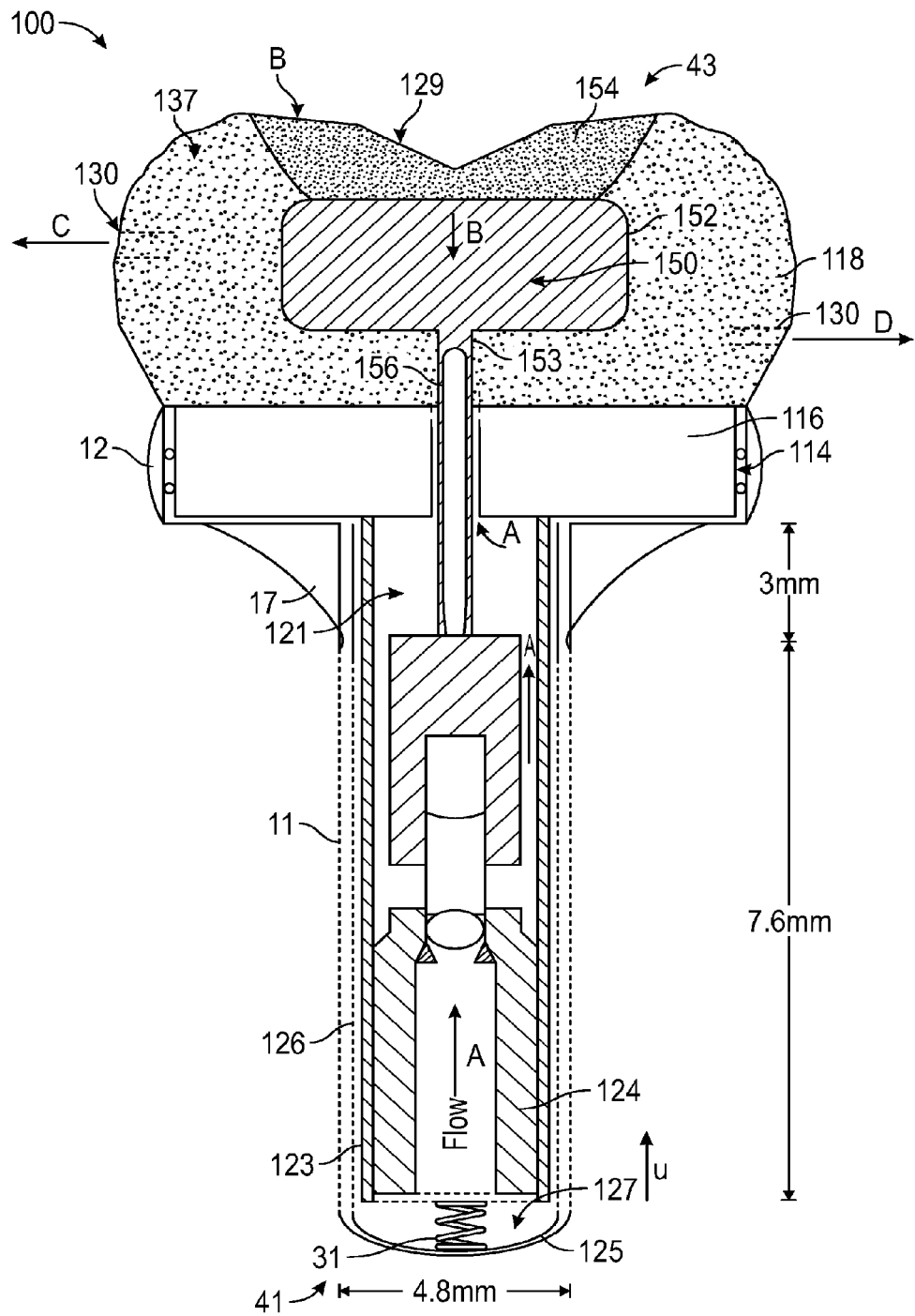
FIG. 6 shows schematic details of another exemplary salivary gland assembly.

In another embodiment and as shown in FIG. 6, exemplary salivary gland assembly 100 includes a crown member 118 mounted on the coronal end 43 of head portion 116 of insert member 114.

In such embodiment, insert member 114 is substantially cylindrical and includes enlarged coronal cylindrical head portion 116 and an apical cylindrical portion 125 extending from head portion 116, the insert member 114 also having a hollow internal chamber 121 configured to house valve member 124 (e.g., check-valve 124). Internal chamber 121 can also optionally house treatment materials 32, 35 to alter the chemistry of the interstitial/marrow fluid, as described above.

Hollow cylindrical portion 125 includes porous walls 126, with the hollow cylindrical portion 125 configured and dimensioned to house the internal chamber 121, and with the cylindrical portion 125 defining an outer chamber 127 between the porous walls 126 and the non-porous walls 123 of internal chamber 121. As similarly discussed above, insert member 114 is configured and dimensioned to be disposed or housed in the hollow implant member 12 (e.g., with the insert member 114 screwed/threaded or snap-fit into the implanted implant member 12).

Internal chamber 121 can be substantially cylindrical and include non-porous walls 123, and be in fluid communication with a valve member 124 near the apical end 41, and be in fluid communication with head portion 116 and/or crown member 118.

Exemplary crown member 118 includes an internal cavity 150 configured and dimensioned to house a bladder member 152 (e.g., air or fluid-filled bladder member 152). Crown member 118 also includes a central bore 153 in communication with cavity 150, the central bore 153 configured to house at least a portion of piston member 156 (e.g., hydraulically or fluidically-driven piston member 156), the piston member 156 mounted to valve member 124. An occlusal member 154 is mounted on the coronal end of bladder member 152 and/or crown member 118, thereby covering the coronal end of bladder member 152.

In exemplary embodiments, coronal forces due to chewing/swallowing or the like (e.g., user chewing forces in the direction of Arrows B on a coronal surface 129 of occlusal member 154) displace or move bladder member 152 in the direction of Arrows B, thereby moving piston member 156 and valve member 124 in the direction of Arrows B, which thereby pressurizes the outer chamber 127 of the insert member 114, and thereby causing treated fluid flow through the insert member 114 and into an oral cavity of the user. In certain embodiments, when the valve member 124 is moved/displaced in the direction of Arrows B, the springs 31 positioned underneath valve member 124 will compress between valve member 124 and the apical end of outer chamber 127, and/or between valve member 124 and the apical end of implant member 12.

When chewing forces are removed, the upward/apical spring force of spring members 31 in the direction of arrows U displace or move valve member 124 in the direction of Arrow U, thereby closing the valve member 124 and creating a vacuum in the outer chamber 127 of insert member 114, which thereby draws-in fluid (e.g., treated fluid) into the chamber 127 (e.g., via pores of walls 11, 126).

As such, the action of user forces (e.g., chewing/swallowing forces of a user) to a coronal surface 129 of occlusal member 154 causes pressure in chamber 127 to drive the flow of fluid (e.g., interstitial/marrow fluid) through the valve member 124 and into internal chamber 121, and up through the internal chamber 121 in the direction of Arrows A and out into the oral cavity via the fluid channels 130 in the crown member 118 and in the directions of Arrows C, D, as similarly described above in connection with fluid channels 30 of head 16. It is noted that in this embodiment, head portion 16 may or may not include fluid channels 130.

It is noted that advantageous crown member 118 can provide additional volume via chamber 137 to house treatment materials 32 and/or 35 (e.g., soluble species, such as, for example, proteins, xylitol, amorphous calcium phosphate, etc.), as similarly described above.

In another embodiment and as shown in FIGS. 7-13, exemplary salivary gland assembly 200 includes an implant member 212, an abutment member having a crown member 218, an insert member 214 having a filter member 264 mounted thereto, a piston member 256, and an occlusal member 254.

Figure 8:
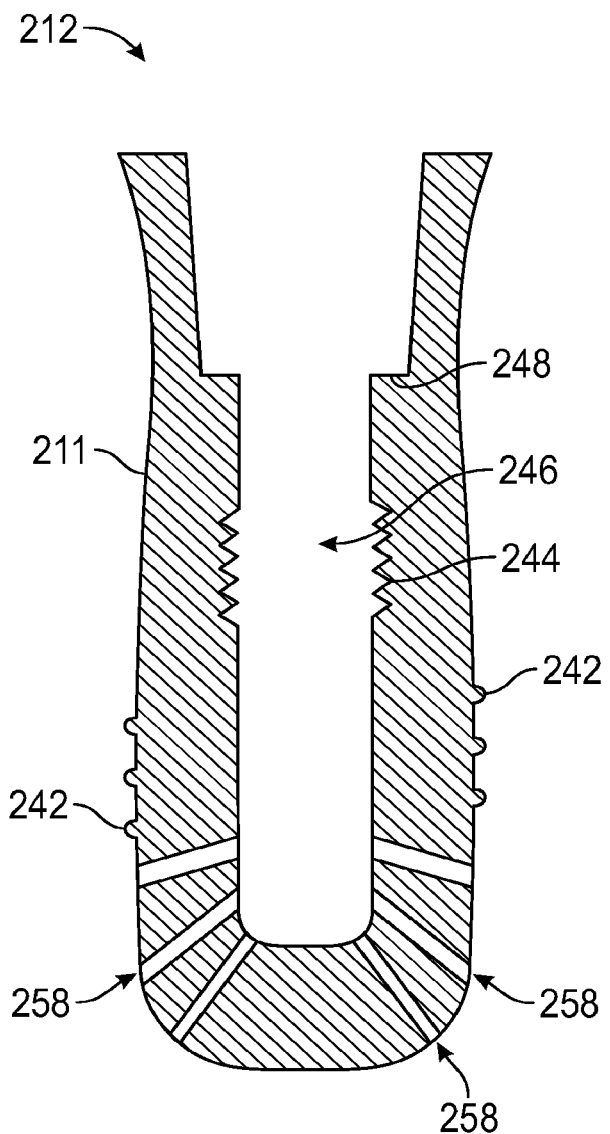
FIG. 8 shows details of an exemplary implant member of the assembly of FIG. 7.

Exemplary implant member 212 is substantially cylindrical and includes pores 258 through wall 211, the wall 211 having external threads 242 (e.g., for implanting purposes) and internal threads 244 (FIG. 8). In certain embodiments and as shown in FIG. 8, implant member 212 includes internal cavity 246 and abutment surface 248. Similar to implant 12, implanted implant member 212 can osseointegrate with mandibular or maxillary bone as a dental implant.

Figure 9:
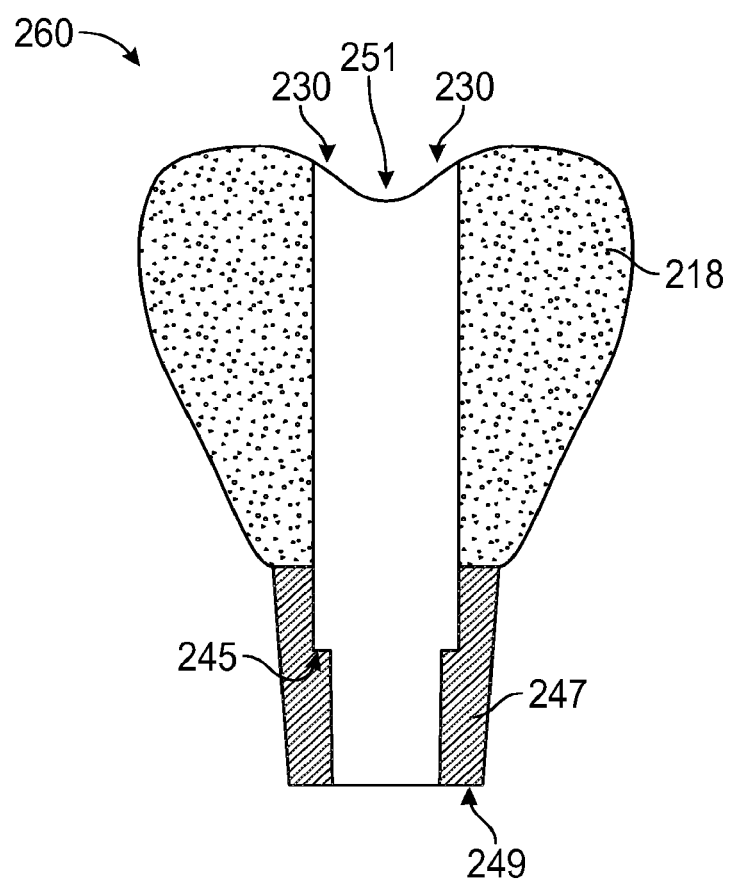
FIG. 9 shows details of an exemplary abutment/artificial crown member configured for an internal piston of the assembly of FIG. 7.

As shown in FIG. 9, abutment/crown member 260 includes abutment portion 247 and crown member 218 mounted to abutment portion 247. In some embodiments, abutment portion 247 may not have crown member 218 mounted thereon. Exemplary abutment portion 247 includes abutment surface 249 at the apical end of abutment portion 247, and includes receiving surface 245, as discussed further below. Abutment member 260 also includes central bore 251, and one or more fluid channels 230.

Exemplary insert member 214 is substantially cylindrical and includes enlarged coronal cylindrical head portion 216 and an apical cylindrical portion 225 extending from head portion 216, the insert member 214 also having a hollow internal chamber 221 configured to house valve member 224 and internal piston member 257. Exemplary piston member 257 is mounted to valve member 224.

Insert member 214 also includes external threads 255, and a filter member 264 (e.g., filter membrane cartridge member 264) is configured and dimensioned to be mounted to the apical end of insert member 214 (e.g., via a snap-fit or the like). The coronal end of insert member 214 can include a receiving cavity 259, as discussed further below. Exemplary head portion 216 serves as a stop for the attachment of this member 214 to the implant member 212 and may include one or more fluid channels 258 therethrough.

Figure 10:
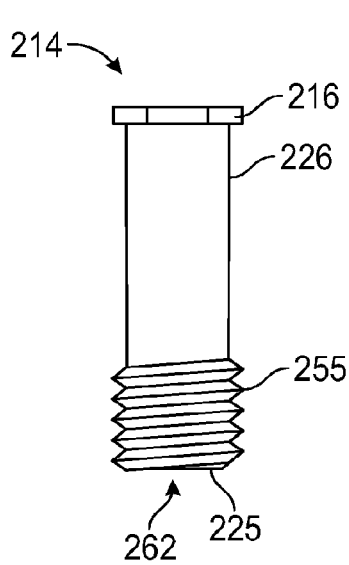
FIG. 10 is a side view of an exemplary insert member of the assembly of FIG. 7.

Hollow cylindrical portion 225 includes wall 226, with one or more pores or openings 262 through wall 226 (e.g., at the apical end—FIG. 10). The cylindrical portion 225 defines an outer chamber 227 between wall 226 and internal piston member 257. As discussed further below, insert member 214 is configured and dimensioned to be disposed or housed in the hollow implant member 212.

Figure 7:
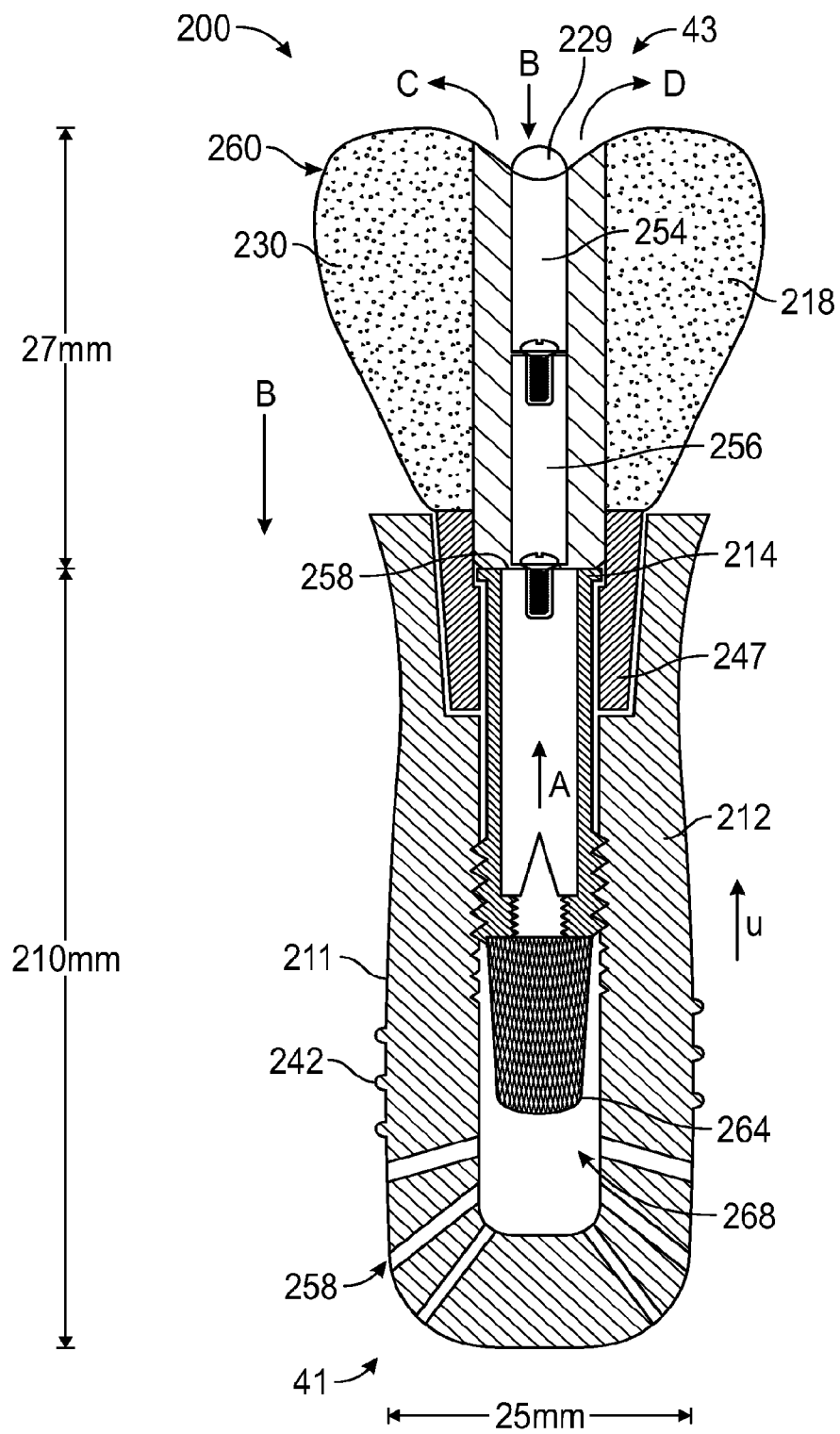
FIG. 7 shows schematic details of another exemplary salivary gland assembly.

As shown in FIGS. 7-9, abutment member 260 is configured to be positioned within internal cavity 246 (FIG. 8) of implant member 212 so that the abutment surface 249 (FIG. 9) of abutment member 260 abuts or contacts the abutment surface 248 (FIG. 8) of implant member 212 (FIG. 7).

Figure 11:
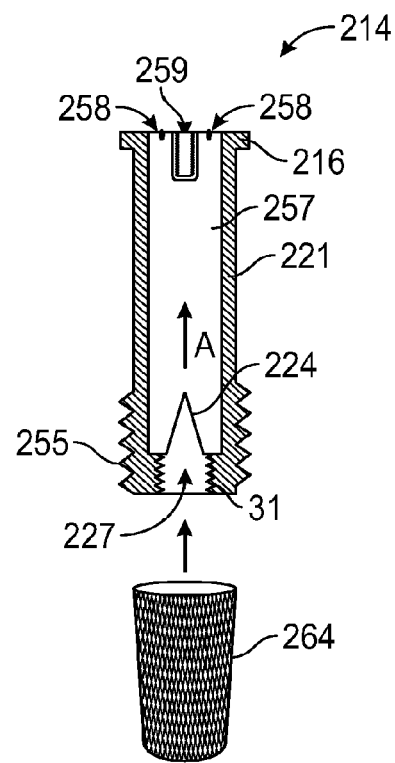
FIG. 11 shows details of the insert member of FIG. 10, prior to mounting filter member to insert member.
Figure 12:
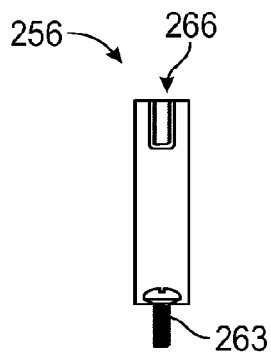
FIG. 12 shows details of an exemplary piston member of the assembly of FIG. 7.
Figure 13:
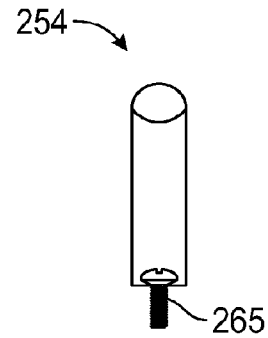
FIG. 13 shows details of an exemplary occlusal member of the assembly of FIG. 7.

As shown in FIG. 11, exemplary insert member 214 (with filter member 264 mounted thereon) can be inserted through central bore 251 of abutment member 260 until head portion 216 rests on receiving surface 245 of abutment member 260, and so that external threads 255 of insert member 214 can be threadably connected to internal threads 244 of implant member 212, thereby securing abutment member 260, insert member 214 and implant member 212 to one another (FIG. 7).

The piston member 256 can then be inserted into cavity 251, and the piston member 256 can be mounted to insert member 214 via a fastener member 263 positioned/secured in receiving cavity 259. The occlusal member 254 can then be inserted into cavity 251, and the occlusal member 254 can be mounted to piston member 256 via a fastener member 265 positioned/secured in receiving cavity 266. In some embodiments, it is noted that assembly 200 may not include occlusal member 254, and the piston member 256 may extend to the coronal end of crown member 218 of assembly 200.

In exemplary embodiments, coronal forces due to chewing/swallowing or the like (e.g., user chewing forces in the direction of Arrows B on a coronal surface 229 of occlusal member 254) displace or move occlusal member 254 and piston member 256 in the direction of Arrows B, thereby moving internal piston member 257 and valve member 224 in the direction of Arrows B, which thereby pressurizes the outer chamber 227 of the insert member 214, and thereby causing fluid flow through the insert member 214 and into an oral cavity of the user. In certain embodiments, when the valve member 224 is moved/displaced in the direction of Arrows B, the springs 31 positioned underneath valve member 224 will compress between valve member 224 and the apical end of outer chamber 227.

When chewing forces are removed, the upward/apical spring force of spring members 31 in the direction of arrow U displace or move valve member 224 in the direction of Arrow U, thereby closing the valve member 224 and creating a vacuum in the outer chamber 227 of insert member 214, which thereby draws-in fluid (e.g., treated fluid) into the chamber 227 and/or into reservoir 268 of implant member 212 (e.g., via pores 258 of wall 211). It is noted that reservoir 268 may be associated with (e.g., lined with) a membrane/filter (e.g., a millipore membrane/filter or the like).

As such, the action of user forces (e.g., chewing/swallowing forces of a user) to a coronal surface 229 of occlusal member 254 causes pressure in chamber 227 to drive the flow of fluid (e.g., interstitial/marrow fluid) through the valve member 224 and into internal chamber 221, and up through the internal chamber 221 in the direction of Arrow A and out into the oral cavity via the fluid channels 258 in insert member 214, and via fluid channels 230 in abutment/crown member 260, and in the directions of Arrows C, D, as similarly described above in connection with fluid channels 30 of head 16.

The present disclosure will be further described with respect to the following examples; however, the scope of the disclosure is not limited thereby. The following examples illustrate fabrication and use of the advantageous salivary gland assemblies.

Example 1

Based on results from an in vivo rabbit study it is noted that: (i) sufficient interstitial/marrow fluid exists for the exemplary assemblies (e.g., assemblies 10, 100, 200) to work, likely with only one implant/assembly (e.g., 10, 100, 200) needed per patient; (ii) there is some positive fluid pressure available necessitating a lower vacuum pressure in the assembly (e.g., 25% to 50% of atmospheric was sufficient to extract 0.05 milliliters of fluid per minute); (iii) the implant wall (e.g., wall 11) does not need to be significantly porous, a limited number of small holes (e.g. approximately 30 holes at 0.5 mm diameter in wall 11) may be sufficient; (iv) holes in wall 11 may not need to be obturated at the first surgery.

Figure 14:
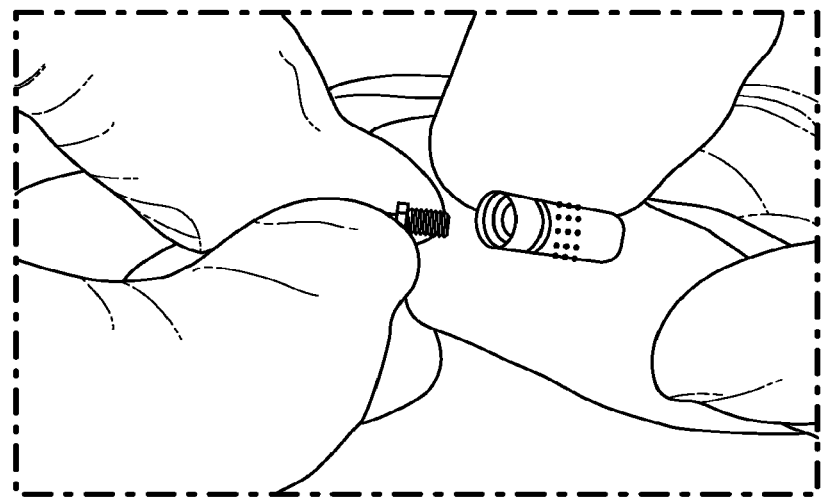
FIGS. 14-17 are images showing an exemplary salivary gland assembly used in a rabbit study.
Figure 15:
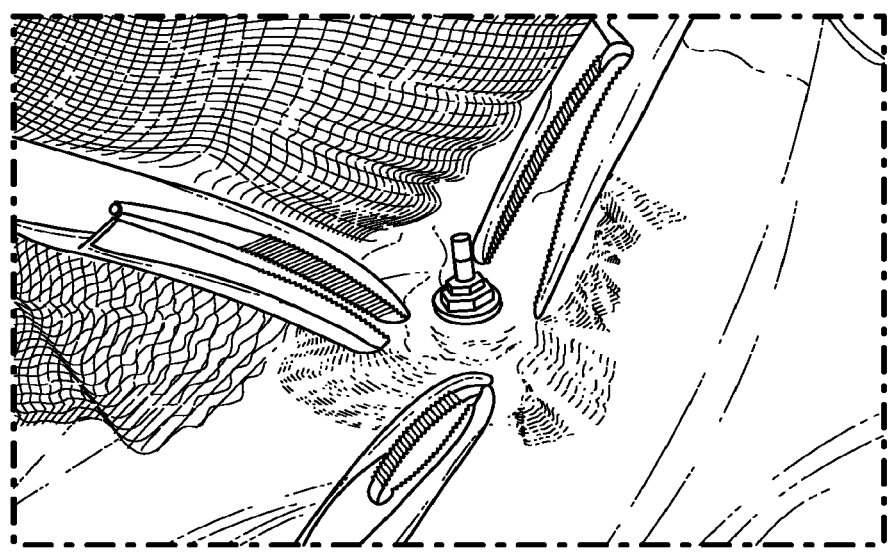

FIGS. 14-17 are photos/images showing an exemplary prototype used in an initial rabbit study. These prototypes were made in a machine shop by hollowing-out an implant member (e.g., Straumann implant, 12 mm, 4.1 mm), adding holes in the endosseous portion, and threads in the coronal portion to accept a custom-made cap having a hole. As shown in FIG. 14, teflon tape was used to seal the system against blood flowing into the tube from soft tissues during the second surgery.

The hole in the cap/crown was filled with a plastic tube plugged with a gutta percha point. The plastic tube was used to help keep blood from filling the implant/assembly, and to facilitate locating the implant/assembly in subsequent surgeries.

Figure 16:
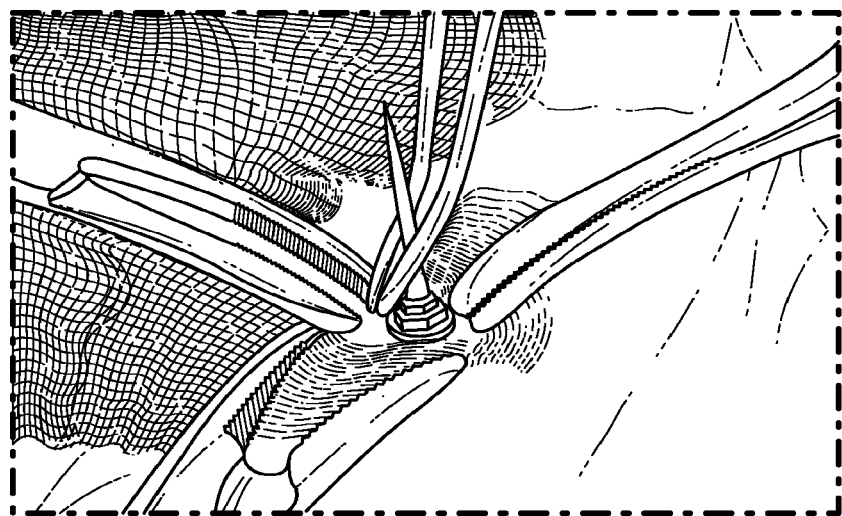

In a first surgery to explore for fluid in the rabbit mandible, absorbent paper points were utilized, such as those used in endodontics (FIG. 16). These were weighed, inserted for 30 s to 60 s and then re-weighed. After approximately 1 month following implantation, the assemblies were providing a few microliters of fluid. This amount may have been due to the holes still being plugged or the need for some vacuum (or both).

Figure 17:
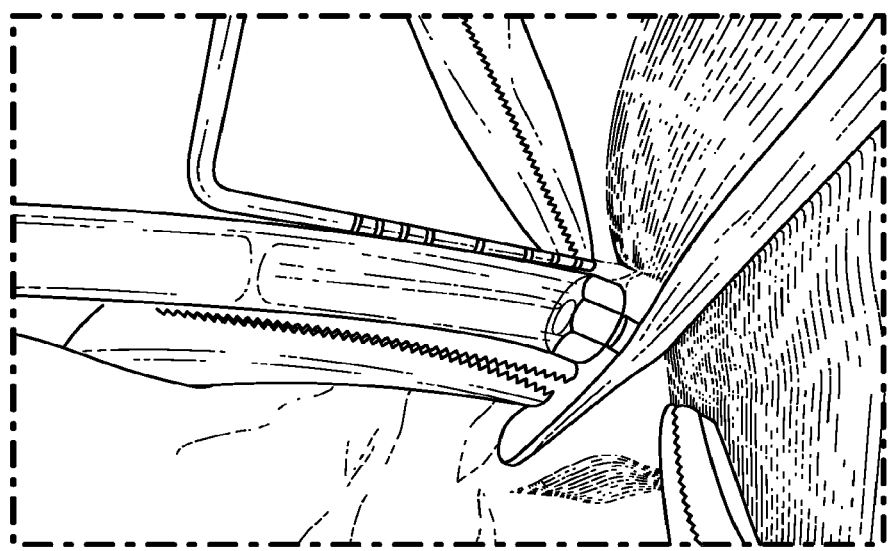

At the last surgery, approximately 3 months following implantation in the rabbit mandible, fluid spontaneously flowed. Under vacuum, it was possible to collect fluid. FIG. 17 shows 8 mm of interstitial fluid inside a 3 mm inside-diameter tube (57 $mm^3$ or 0.057 ml collected in under 5 seconds at 0.75% to 0.5% atmospheric pressure).

The ranges disclosed herein are inclusive of the endpoints, and the endpoints are independently combinable with each other. Each range disclosed herein constitutes a disclosure of a point or sub-range lying within the disclosed range.

The use of the terms "a" and "an" and "the" and words of a similar nature in the context of describing the improvements disclosed herein (especially in the context of the following claims) are to be construed to cover both the singular and the plural, unless otherwise indicated herein or clearly contradicted by context. Further, it should further be noted that the terms "first," "second," and the like herein do not denote any order, quantity, or relative importance, but rather are used to distinguish one element from another. The modifier "about" used in connection with a quantity is inclusive of the stated value and has the meaning dictated by the context (e.g., it includes, at a minimum the degree of error associated with measurement of the particular quantity).

The methods described herein can be performed in a suitable order unless otherwise indicated herein or otherwise clearly contradicted by context. The use of the examples, or exemplary language (e.g., "such as"), is intended merely to better illustrate the disclosure and does not pose a limitation on the scope of the disclosure or embodiments thereof unless otherwise claimed.

Unless defined otherwise, the technical and scientific terms used herein have the same meaning as is commonly understood by one of skill in the art to which this disclosure belongs.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications and substitutions are intended in the foregoing disclosure. Accordingly, it is appropriate that the appended claims be construed broadly and in a manner consistent with the scope of the disclosure.

What is claimed is:

1. A method for harvesting fluid comprising:
   disposing an implant member within a mouth of a user;
   disposing an insert member at least partially within the implant member; and
   capturing and harvesting existing fluid of the user as replacement saliva to the user via the implant member and the insert member;
   wherein the fluid is interstitial fluid or marrow fluid.

2. The method of claim 1, wherein the implant member is configured and dimensioned to be at least partially implanted in mandibular or maxillary bone of the user; and
   wherein the implant member and the insert member utilize fluid from within the mandibular or maxillary bone as the replacement saliva for the user.

3. The method of claim 1, wherein the implant member and the insert member include porous walls to harvest the fluid; and
   wherein the insert member is configured to screw or snap fit into the implant member.

4. The method of claim 1, wherein the insert member includes a piston member, the piston member configured to be driven, at least in part, by tooth contact forces of the user to harvest the fluid as the replacement saliva for the user.

5. The method of claim 4, wherein the piston member is driven, at least in part, by masticatory forces or incidental tooth contact during swallowing forces of the user on the piston member to harvest the fluid as the replacement saliva for the user.

6. The method of claim 1, wherein the insert member includes treatment materials to adjust or alter the chemistry of the fluid; and
   wherein the treatment materials include semi-permeable membranes or soluble particles.

7. The method of claim 4, wherein the piston member is a piston head; and
   wherein the piston head is in fluid communication with a one-way valve.

8. The method of claim 4, wherein the piston member utilizes the tooth contact forces of the user to: (i) harvest the fluid, (ii) drive the fluid to flow through treatment materials to alter or adjust the chemistry of the fluid, and (iii) drive the fluid to an oral cavity of the user.

9. The method of claim 1, wherein the implant member is substantially hollow and the insert member is removable and replaceable from the implant member.

10. The method of claim 1, wherein the insert member includes an outer chamber in fluid communication with the fluid; and
    wherein when tooth contact forces of the user engage the insert member, the outer chamber is pressurized, thereby causing fluid to flow through the insert member and out of an outlet of the insert member and into an oral cavity of the user.

11. The method of claim 10 further comprising a valve member associated with the insert member; and
    wherein when the tooth contact forces cease engaging the insert member, the valve member closes and creates a vacuum in the outer chamber, thereby drawing additional fluid of the user into the outer chamber.

12. The method of claim 11, wherein the insert member includes one or more spring members; and
    wherein when the tooth contact forces cease engaging the insert member, the one or more spring members facilitate the closing of the valve member.

13. The method of claim 1 further comprising a crown member mounted with respect to the insert member, the crown member providing a coronal chewing surface for the user, and providing a chamber configured to house or treat the fluid.

14. The method of claim 1, wherein the insert member includes a fluidically-driven piston member in communication with a fluid bladder member of a crown member, the fluid bladder member having an occlusal member mounted on a coronal end of the fluid bladder member; and
    wherein the fluidically-driven piston member is configured to be driven, at least in part, by tooth contact forces of the user on the occlusal member to harvest the fluid as the replacement saliva for the user.

15. The method of claim 1 further comprising a filter member mounted to an apical end of the insert member, wherein the filter member is in communication with a fluid reservoir of the implant member.

16. The method of claim 1 further comprising an abutment member, the abutment member configured to be at least partially disposed within the implant member, with the insert member configured to be at least partially disposed within the abutment member and at least partially disposed within the implant member to secure the abutment member, the insert member and the implant member to one another.

17. The method of claim 16 further comprising a crown member mounted on a coronal end of the abutment member, and a piston member mounted on a coronal end of the insert member, the piston member configured to be driven, at least in part, by tooth contact forces of the user to harvest the fluid as the replacement saliva for the user.

18. The method of claim 16, wherein the insert member is threadably engaged with the implant member to secure the abutment member, the insert member and the implant member to one another.

19. A dental implant assembly comprising:
an implant member, the implant member configured and dimensioned to be at least partially disposed within a mouth of a user; and
an insert member at least partially disposed within the implant member;
wherein the implant member and the insert member are configured and dimensioned to capture and harvest existing fluid of the user as replacement saliva to the user; and
wherein the fluid is interstitial fluid or marrow fluid.

20. The dental implant assembly of claim 19, wherein the implant member is configured and dimensioned to be at least partially implanted in mandibular or maxillary bone of the user; and
wherein the implant member and the insert member utilize fluid from within the mandibular or maxillary bone as the replacement saliva for the user.

* * * * *